United States Patent
Zhong et al.

(10) Patent No.: US 9,669,054 B2
(45) Date of Patent: Jun. 6, 2017

(54) PH BUFFERED BIOACTIVE GLASS, AND ITS PREPARATION PROCESS AND USE

(71) Applicant: CHANGZHOU BIO-SHENG TECHNOLOGY CO., LTD., Jiangsu (CN)

(72) Inventors: Jipin Zhong, Jiangsu (CN); Yongxiang Wang, Shanghai (CN); Jiang Chang, Shanghai (CN); Yuhong Xu, Shanghai (CN)

(73) Assignee: Changzhou Bio-Sheng Technology Co., LTD, Jiangsu (CN)

( * ) Notice: Subject to any disclaimer, the term of this patent is extended or adjusted under 35 U.S.C. 154(b) by 435 days.

(21) Appl. No.: 14/345,806

(22) PCT Filed: Sep. 20, 2012

(86) PCT No.: PCT/CN2012/081643
§ 371 (c)(1),
(2) Date: Mar. 19, 2014

(87) PCT Pub. No.: WO2013/041030
PCT Pub. Date: Mar. 28, 2013

(65) Prior Publication Data
US 2014/0227365 A1    Aug. 14, 2014

(30) Foreign Application Priority Data
Sep. 20, 2011   (CN) .......................... 2011 1 0282549

(51) Int. Cl.
*A61K 33/00*     (2006.01)
*A61K 33/24*     (2006.01)
(Continued)

(52) U.S. Cl.
CPC ............ *A61K 33/24* (2013.01); *A61K 31/194* (2013.01); *A61K 33/00* (2013.01); *A61K 33/08* (2013.01);
(Continued)

(58) Field of Classification Search
None
See application file for complete search history.

(56) References Cited

U.S. PATENT DOCUMENTS

| 5,643,789 A * | 7/1997 | Ducheyne ................. A61F 2/28 424/422 |
| 5,762,950 A * | 6/1998 | Yli-Urpo ............. A61K 9/0024 424/422 |
| 2007/0258916 A1 | 11/2007 | Ferracane |

FOREIGN PATENT DOCUMENTS

| CN | 1455661 | 11/2003 |
| CN | 1636576 | 7/2005 |

(Continued)

OTHER PUBLICATIONS

Lei et al. (Biomedical Materials 2010, vol. 5, No. 5).*
(Continued)

*Primary Examiner* — Abigail Fisher
*Assistant Examiner* — Jessica Kassa
(74) *Attorney, Agent, or Firm* — Kirschstein, Israel, Schiffmiller & Pieroni, P.C.

(57) ABSTRACT

The present invention relates to a pH buffered bioactive glass, and its preparation process and use. The pH buffered bioactive glass comprises $SiO_2$, $CaO$, $Na_2O$, and $P_2O_5$, and further comprises solid acidic particles or a Tris buffer solution. The pH buffered bioactive glass can regulate the pH of formulations comprising bioactive glass, and has a good therapeutic effect with a low dosage.

5 Claims, 2 Drawing Sheets

(51) Int. Cl.
    *A61K 33/42*    (2006.01)
    *A61K 33/08*    (2006.01)
    *A61K 31/194*   (2006.01)
    *C03C 4/00*     (2006.01)
    *A61K 9/10*     (2006.01)

(52) U.S. Cl.
    CPC ............ *A61K 33/42* (2013.01); *C03C 4/0007* (2013.01); *A61K 9/10* (2013.01)

(56)        References Cited

FOREIGN PATENT DOCUMENTS

CN          1279924 C       10/2006
CN          102258432       11/2011

OTHER PUBLICATIONS

M. Gubler, T.J. Brunner, M. Zehnder, T. Waltimo, B. Sener, W.J. Stark, "Do bioactive glasses convey a disinfecting mechanism beyond a mere increase in pH?", International Endodontic Journal, vol. 41, pp. 670-678, 2008.

J.E. Rectenwald, R.M. Minter, J.J. Rosenberg, G.C. Gaines, S. Lee, L.L. Moldawer,"Bioglass attenuates a proinflammatory response in mouse peritoneal endotoxicosis", Shock, vol. 17 (2): pp. 135-138, 2002.

T. Watanabe, T. Arakawa, T. Fukuda, K. Higuchi, and K. Kobayashi, "Role of neutrophils in a rat model of gastric ulcer recurrence caused by interleukin-1 beta", Am. J. Pathol., vol. 150: pp. 971-979, 1997.

Cerruti, et al., "Effect of pH and Ionic Strength on the Reactivity of Bioglass", Biomaterials, vol. 26, No. 14, pp. 1665-1674, May 1, 2005.

Cerruti, et al., "An Analytical Model for the Dissolution of Different Particle Size Samples of Bioglass in TRIS-buffered Solution", Biomaterials, vol. 26, No. 24, pp. 4903-4911, Aug. 1, 2005.

Moosvi, et al., "Bioactive Glass Modulation of Intestinal Epithelial Cell Restitution", Acta Biomateriala, vol. 5, No. 1, pp. 76-83, Jan. 1, 2009.

European Search Report, corresponding European Appl. No. 12832898, Mar. 15, 2016.

* cited by examiner

PH BUFFERED BIOACTIVE GLASS, AND ITS PREPARATION PROCESS AND USE

The present invention depends on and claims a priority of a Chinese patent application 201110282549.0 filed on Sep. 20, 2011, which is incorporated herein by reference in its entirety.

FIELD OF THE INVENTION

This invention relates to a pH buffered bioactive glass, and its preparation process and use.

BACKGROUND OF THE INVENTION

In China and all over the world, 10% people are patients suffering from gastropathy, which, according to statistics, are one of the three largest groups of patients. Gastric and duodenum ulcers have an extremely high recurrence rate after being cured, and the natural course thereof can last for 8 to 10 years. The long term use of medicines is an important measure for controlling gastric and duodenum ulcers, and now, a few tens of drugs are commonly being used, which can be categorized into three groups, namely, antacids, mucosa protectors and antibiotics. However, drugs which can promote the growth of soft tissue and cells, and directly repair and heal gastric mucosa tissue wounds (namely, gastric ulcers) thereby resulting in a permanent cure are not available in the drug market. Currently available drugs in fact do not thoroughly heal gastric mucosa ulcer wound, but only play a role in protecting and maintaining a good environment, and leave ulcer healing to the patient's self-healing ability. As a result, the ulcer heals slowly on the one hand, and on the other hand, for a patient having low self-healing ability, the ulcers cannot completely heal, resulting in a high recurrence rate and longer course. Reference document 1 reported that bioactive glass can promote the growth of mucosa epithelial cells, and has a direct repairing and healing effect on mucosa tissue wounds (namely, ulcers), so as to lead to a permanent cure for gastric and duodenum ulcers, while quickly increasing pH to neutralize the acid environment at a liquid condition, so as to produce an environment good for healing gastric ulcers. Currently available drugs lack the above mentioned properties. These properties can greatly improve efficiency of drug treatment, shorten the time for the treatment and reduce the recurrence rate of ulcers. However, Reference document 1 does not report any specific safest and most effective bioactive glass formulation.

Moreover, bioactive glass can rapidly increase the pH of a liquid up to 12. Such a high-alkaline pH could make new drug unsafe and may cause some harmful effects on living tissues and organs.

Reference document 1: a Chinese patent CN1279924C

SUMMARY OF THE INVENTION

With further experiments and studies, the inventors found that the composition of a bioactive glass has considerable influence on the safety and treatment efficiency thereof. The inventors also discovered the optimum formulation of a bioactive glass which is the safest and most effective for the treatment of gastric and duodenum ulcers.

Regarding the above problem, the present invention provides a pH buffered bioactive glass, which can regulate the pH of the formulated bioactive glass, and has a good therapeutic effect with a low dosage.

The technical methods adopted by the present invention are described as follows:

A pH buffered bioactive glass, characterized in that said pH buffered bioactive glass is a composition A comprising a bioactive glass and solid acidic particles, or a composition B comprising a bioactive glass and a Tris buffer solution, wherein said bioactive glass comprises $SiO_2$, CaO, $Na_2O$ and $P_2O_5$ as the raw materials, the content of each raw material in said composition A is measured by "part by mass", and the content of each raw material in said composition B is measured by "gram per 100 ml of Tris", Composition A: $SiO_2$-40 to 60; CaO-15 to 30; $Na_2O$-15 to 30; $P_2O_5$-2 to 8; Solid acidic particles-3 to 7;

Composition B: $SiO_2$-0.0003 to 22.5 g; CaO-0.0001 to 12.25 g; $Na_2O$-0.0001 to 12.25 g; $P_2O_5$-0.00004 to 3 g, based on 100 ml of the Tris buffer solution, wherein the pH thereof is finally adjusted to 8.0±0.3.

The pH buffered bioactive glass of the present invention can buffer a local surge in pH (up to 12) caused by the surface reaction of pure bioactive glass ($SiO_2$, CaO, $Na_2O$, $P_2O_5$ and $B_2O_3$) particles, so as to achieve a therapeutic effect and ensure drug safety. Moreover, the median effective dose $ED_{50}$ of the pH buffered bioactive glass of the present invention for treating chronic gastric ulcers is only 0.4 mg/kg/d, which is ⅓ of the median effective dose of the currently one of the best drugs, omeprazole (the $ED_{50}$ thereof is 1.3 mg/kg/d).

The pH buffered bioactive glass of the present invention has an effect equivalent to that of a currently available representative drug (hydrotalcite) with respect to the prevention of stress-induced gastric ulcers (administration for the purpose of prevention); compared with other drugs, it shows more significant effectiveness in treating chronic gastric ulcers (administration for the purpose of treatment) and in preventing recurrence of chronic gastric ulcers, and demonstrates higher efficiency (a small dose can also achieve the optimum effect). The above features also indicate the repairing and healing effect of the pH buffered bioactive glass of the present invention on ulcer areas.

The present invention also relates to a method for preparing the pH buffered bioactive glass, comprising:

1) a step of melting said raw materials in said ratios at high temperature to form a bioactive glass; and 2) evenly mixing the above-obtained bioactive glass with the solid acidic particles (composition A) in said ratio, or the Tris buffer solution (composition B) in said ratio to obtain said pH buffered bioactive glass.

The present invention further relates to a use of the pH buffered bioactive glass in the preparation of a medicine for preventing and treating gastric and duodenum ulcers and/or in the preparation of a medicine for preventing recurrence of gastric and duodenum ulcers.

DESCRIPTION OF THE EMBODIMENTS

Figure 1:
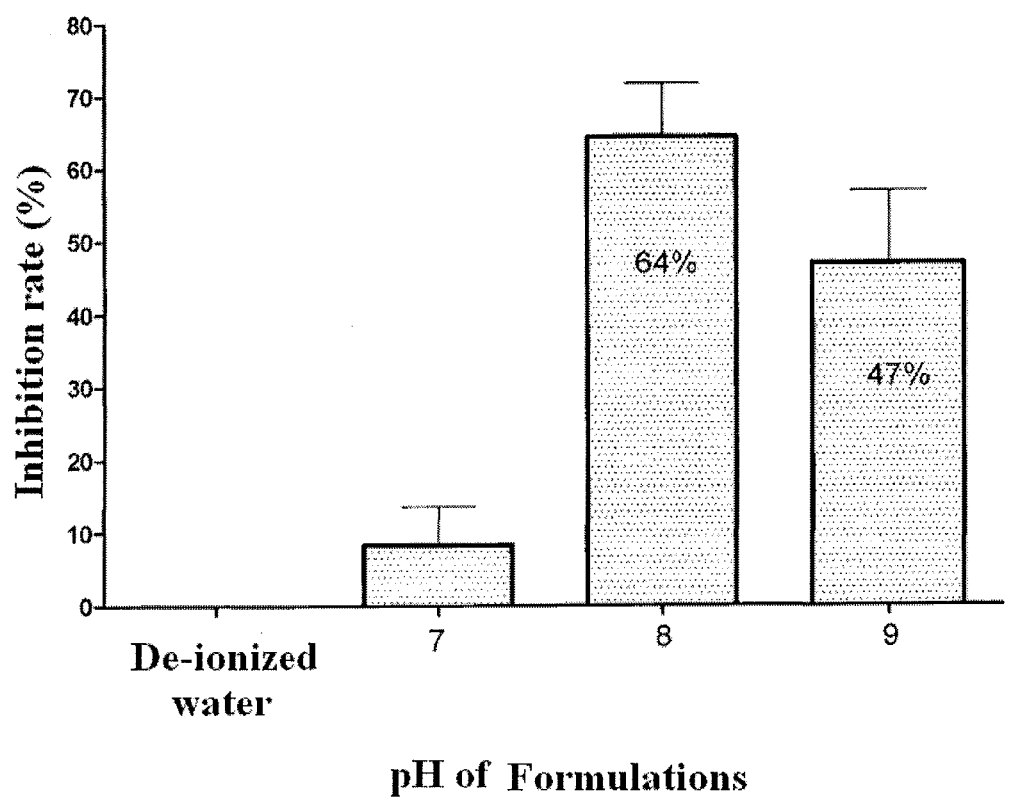
FIG. 1 and FIG. 2 are drawings showing the technical features of the pH buffered bioactive glass in Experiment Example 2 (experiment on pH vs. inhibition effect on stress-induced gastric ulcers).

The following are detailed descriptions of the embodiments of the present invention based on the Examples. The content ratio or percentage in the present invention is measured by mass unless otherwise specified. Exception: the content percentage in the pH buffered bioactive glass of composition B is measured by gram of the contained raw materials per 100 ml of Tris. The pH buffered bioactive glass of the present invention is hereinafter referred to as "Weibeisheng".

It has been reported that bioactive glass can promote the growth of epithelial cells, and the growth and healing of soft tissues, and it has a direct repairing and healing effect on mucosa tissue wounds (namely, ulcers), so as to have a permanent cure for gastric and duodenum ulcers. Bioactive glass powder which is attached to the surface of gastric mucosa and the ions released from bioactive glass which are attached to the surface of gastric mucosa can promote the growth of mucosa epithelial cells and directly repair and heal ulcers.

The pH buffered bioactive glass of the present invention as shown in the technical solution of the claims can buffer a local surge in pH (up to 12) caused by the surface reaction of pure bioactive glass ($SiO_2$, CaO, $Na_2O$, $P_2O_5$ and $B_2O_3$) particles, so as to achieve the therapeutic effect and ensure drug safety. Moreover, the median effective dose $ED_{50}$ of the pH buffered bioactive glass of the present invention for treating chronic gastric ulcers is only 0.4 mg/kg/d, which is 3 times less than the median effective dose of the one of the currently best drugs, omeprazole (the $ED_{50}$ thereof is 1.3 mg/kg/d). It's worth to point out that the effectiveness of the pH buffered bioactive glass of the present invention in treating chronic gastric ulcers exceeds our expectations (the $ED_{50}$ is 0.4 mg/kg/d, and 3 mg/kg/d can achieve the maximum efficacy).

In the pH buffered bioactive glass of the present invention, said solid acidic particles may be commonly-used solid acidic particles without any toxic or side effects. Since the composition is applied to treatment of gastric and duodenum ulcers, the solid acidic particles therein are preferably solid citric acid particles ($C_6H_8O_7$) or titanium oxide-based solid acidic particles ($SO_4^{2-}/TiO_2$), and most preferably are solid citric acid particles.

In the pH buffered bioactive glass of the present invention, said Tris buffer solution may be prepared by commonly-used methods in the art. For example, said Tris buffer solution may be prepared as described below: to a mixture of 700 ml of deionized water, 6.069 g of Tris powder and 35 ml of HCl (1N), deionized water was added by using a constant volume method to reach 1000 ml, and a pH value of 7.23. A Tris buffer solution may be prepared by methods in an enlarged or a reduced proportion to the above method.

In the pH buffered bioactive glass of the present invention, the pH of composition A and that of composition B in a liquid are about 8 (8.0±0.3). The pH of composition A is adjusted by the solid acidic particles, while the pH of composition B is adjusted by the Tris buffer solution in combination with a pH modifier. The pH modifier may be a conventional pH modifier in the art, for example, hydrochloric acid. To be more specific, the pH of composition B of the pH buffered bioactive glass of the present invention can be adjusted by 1N of hydrochloric acid to 8.0±0.3.

EXAMPLES

Production Examples

The first four components as listed in Table 1 below were melted at high temperature, and then were evenly mixed with solid acidic particles in an amount as shown in Table 1 below or with the Tris buffer solution in an amount as shown in Table 2 below to obtain the pH buffered bioactive glass of the present invention. The amount as shown in Table 1 is measured by "part by mass".

TABLE 1

| Component Amount | Production Ex. 1 | Production Ex. 2 | Production Ex. 3 | Production Ex. 4 | Production Ex. 5 | Production Ex. 6 | Production Ex. 7 | Production Ex. 8 |
|---|---|---|---|---|---|---|---|---|
| $SiO_2$ | 45 | 40 | 41.85 | 50 | 60 | 40 | 50 | 60 |
| CaO | 24.5 | 30 | 22.78 | 20 | 15 | 30 | 20 | 15 |
| $Na_2O$ | 24.5 | 20 | 22.78 | 30 | 15 | 20 | 30 | 15 |
| $P_2O_5$ | 6 | 5 | 5.58 | 2 | 8 | 5 | 2 | 8 |
| Solid citric acid particles | 0 | 7 | 7 | 3 | 5 | 0 | 4 | 0 |
| Titanium oxide-based solid acidic particles | 0 | 0 | 0 | 0 | 0 | 7 | 3 | 3 |

TABLE 2

| Component Amount | Production Ex. 9 | Production Ex. 10 | Production Ex. 11 |
|---|---|---|---|
| $SiO_2$ (g) | 0.00122 | 0.00900 | 22.5 |
| CaO (g) | 0.00033 | 0.00245 | 12.25 |
| $Na_2O$ (g) | 0.00033 | 0.00245 | 12.25 |
| $P_2O_5$ (g) | 0.00016 | 0.00120 | 3 |
| Tris buffer solution (ml) | 100 | 100 | 100 |

Experiment Example 1

Experiment on pH Versus Acute Toxicity (the pH Buffered Bioactive Glass of Production Example 11 was Used)

Test object: Continuous observation for 14 days of acute toxicity reaction, including death, of mice to the administration of a single intragastric dose (20 g/kg) of bioactive glass particles (including Production Example 1, particles of the bioactive glass containing $SiO_2$, CaO, $Na_2O$ and $P_2O_5$ in given amounts—, hereinafter referred to as particles).

Tested Drugs: Suspension (0.5 g/ml, pH: 12.86) prepared (before use) from particles and normal saline was used in the experiment of the first group; suspension (0.5 g/ml) prepared (before use) from particles and a Tris buffer solution (pH: 7.23) (Production Example 11), wherein HCl (1 N) was added to the suspension to adjust the pH to 8.0, was used in the experiment of the second group.

Tested Animals: 40 male Kunming mice of clean grade, each of which weighs 23-27 g, were put in an animal laboratory and raised for 7 days after purchased.

Method: The 40 mice were divided into two groups, underwent fasting (while water was supplied) for 12 hours before administration, and underwent fasting again for 3 to 4 hours after the tested drugs were administered. To the first group, the suspension (0.5 g/ml, pH: 12.86) prepared from normal saline was intra-gastrically administered, while to the second group, the suspension (0.5 g/ml, pH: 7.25) prepared from a Tris buffer solution was administered. The dose for each group is 20 g/kg, and the volume of the dose is 0.4 ml per 10 g weight of the mouse. The toxicity reaction and death of the animals, including poisoning symptoms, occurrence and development, symptomatic sign and behavior before death and time of death, etc. were continuously observed for 14 days.

Results: After administration, the mice of the first group were dispirited and scarcely moved, one of which continuously hiccupped for about 0.5 hour. 18 hours after administration, one mouse was found dead. Autopsy results showed that the stomach of the mouse was filled up with white contents, intestinal inflation was serious, and no obvious abnormity was found anywhere else. 3 days after administration, two mice died. Autopsy results showed that flatulence was serious in both mice, hepatosplenomegaly was found in one of the mice, and no obvious abnormity was found anywhere else. 4 days after administration, one mouse was found dead. Autopsy results showed hepatosplenomegaly but no obvious abnormity anywhere else. 12 days after administration, two mice were found dead. Autopsy was not conducted because it was too long before the death was found. In the 14 days, 6 mice in total were found dead. The mortality was 30%. No obvious abnormity was found in the rest mice.

After administration, the mice of the second group had good spirits, moved freely, and breathed stably. No obvious abnormity (such as hiccup, vomiting, convulsion, and gatism) and no death were found. The drug suspension (pH: 8) prepared by pH buffering did not cause obvious acute toxicity reaction or death of the mice. The formulation with pH 8 is the safest formulation with a minimal toxicity.

Experiment Example 2

Experiment on pH Versus Stress-Induced Gastric Ulcer Inhibition Effect

We have proved that the bioactive glass has a protection effect on acute gastric ulcers, and the efficacy thereof is related to the pH value, And also, by examining pH 2, 4, 6, 8, 10 and 12, we have found that pH 8 is the best pH value to enable bioactive glass to produce the optimum effect to inhibit gastric ulcer happen. Due to the broad range of the testing pH values, we reduced the range of pH values in further studies and experiments. Also, we have used the model to create gastric ulcer by restraint water-immersion stress and further examined the best pH value which resulted in the most effective inhibition for the gastric ulcer to happen.

The mice were divided into four groups, to which deionized water (the solvent control group), and three kinds of Weibeisheng with pH 7, 8 and 9 at a dose of 1 g/kg were respectively intragastrically administrated. Two hours later, the mice were subjected to stress in water at 21±1° C. for 15 hours, and were administered again two hours before the end of the stress. Then the animals were killed and autopsy was performed. The specific method is described as below: the pylorus and then the cardia of the mice were ligated, so that the stomach was freed; subsequently, 1 ml of 1% neutral formalin solution was injected to the stomach from pylorus; the stomach was cut along the greater curvature after it was placed and fixed in 10% neutral formalin solution for 30 minutes; the contents in the stomach were washed out by 0.9% sodium chloride solution; after that, the stomach was flattened for the inspection of gastric mucosal lesions; the ulcers were scored (graded) and the ulcer inhibition rates were calculated according to the following method.

(1) Grade 0: the mucous membrane is perfect without lesions; (2) Spot ulcers (the mucosal defects with a size of less than 1 mm or bleeding erosive spots): grade 1—punctate bleeding with 1 to 5 spots; grade 2—punctate bleeding with 6 to 10 spots; grade 3—punctate bleeding with 10 spots or more; (3) strip bleeding: grade 4—1 to 5 strips; grade 5—6 to 10 strips; grade 6—10 strips or more; (4) larger ulcers (>3 mm): grade 4—1 larger ulcer; grade 5—two larger ulcers or more; and grade 6—perforated ulcers.

Ulcer inhibition rate=(average score of the model control group−average score of the experimental groups)/average score of the model control group×100%.

As shown in FIG. 1, among the three kinds of Weibeisheng with a pH of 7, 8 and 9 respectively, which are all used at a dose of 1 g/kg, the Weibeisheng with a pH of 7 does not have an inhibition effect on stress-induced gastric ulcers (as compared with the solvent control group, $p>0.05$); the Weibeisheng with a pH of 8 and the Weibeisheng with a pH of 9 both have a significant inhibition effect (as compared with the solvent control group, $p<0.05$), and the inhibition rates are respectively 64% and 47%.

Figure 2:
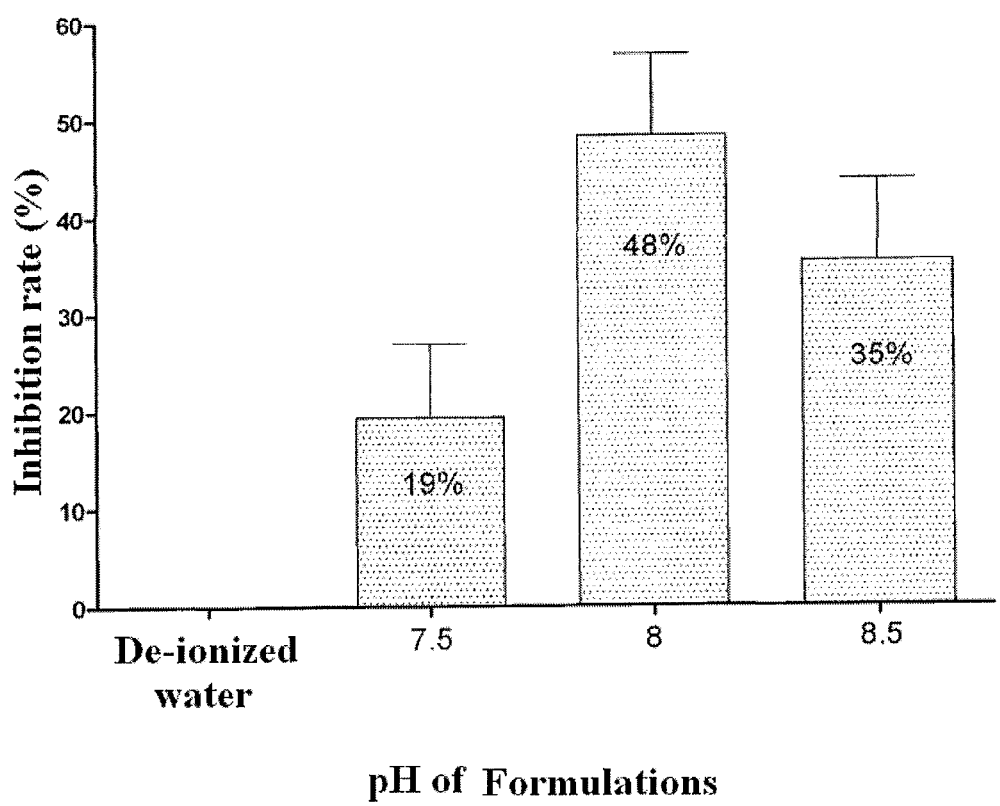

As shown in FIG. 2, the pH values are further restricted to 7.5, 8 and 8.5, the inhibition rates of the three formulations on stress-induced gastric ulcers are respectively 19%, 48% and 35%, and those formulations all have a significant inhibition effect ($p<0.05$) as compared with the solvent control group.

The relative results of the reading of each test in FIG. 1 and in FIG. 2 are consistent.

Conclusion: pH 8 is the optimum pH value for the bioactive glass to inhibit the stress-induced gastric ulcers.

Experiment Example 3

Treatment of Acetic-Acid Induced Chronic Gastric Ulcers in Rats by Using the pH Buffered Bioactive Glass In this study and experiment, we studied the dose-effect relationship of the tested drug (the bioactive glass) by adopting the rat model of acetic-acid induced chronic gastric ulcers, and using hydrotalcite and omeprazole as the positive controls, so as to evaluate the effect of the bioactive glass in the treatment of chronic gastric ulcers. The results showed that the therapeutic effect of the pH buffered bioactive glass on chronic gastric ulcers is equivalent to that of omeprazole (>60%) and is superior to that of hydrotalcite (38%). With respect to the $ED_{50}$ of the three tested drugs in the treatment of chronic gastric ulcers, the amount of the bioactive glass is the least among the three: the $ED_{50}$ (median effective dose) of the bioactive glass is only 0.4 mg/kg (Production Example 9), the $ED_{50}$ of omeprazole is 1.3 mg/kg, and the $ED_{50}$ of hydrotalcite is 1.0 mg/kg.

Conclusion: the bioactive glass of the present invention has a stronger therapeutic effect on acetic-acid induced chronic gastric ulcers in rats.

TABLE 3

Table 3: The $ED_{50}$ and the maximum inhibition rate $E_{max}$ of the bioactive glass of the present invention, omeprazole and hydrotalcite in inhibiting acetic-acid induced chronic gastric ulcers in rats.

|  | Bioactive glass | Omeprazole | Hydrotalcite |
| --- | --- | --- | --- |
| $ED_{50}$ (mg/kg) | 0.4 ± 0.1 | 1.3 ± 0.1 | 1.0 ± 0.2 |
| $E_{max}$ (%) | 64.1 ± 7.6 | 66.2 ± 7.4 | 37.8 ± 5.6 |

Supplement—Rat Model of Acetic-Acid Induced Chronic Gastric Ulcer:

After fasting for 24 hours, the rats were anesthetized and disinfected in a conventional way, and then was cut from the xiphoid down along the medioventral line to about 2 cm, so as to remove the stomach from the enterocoelia; 5 μl of 100% glacial acetic acid was injected by using a microsyringe into a position close to the muscular layer below the anterior wall serosa of the gastric antrum; when a translucent white spot with a diameter of about 3 mm appeared, the stomach was given back to the enterocoelia, and was enveloped in omentum majus; then, peritoneum, muscular layer and skin were sutured in this order.

Each drug was divided into 5 groups according to the administration method described above, namely, a model group and four groups with different doses of drugs. Each group of the drugs was administered to 6 to 8 mice. At the third day after the surgery, the treatment started by intragastrically administering drugs to the rats once a day for 7 days, wherein normal saline was administered in the same volume to the rats in the model group instead. The doses of the drugs in each group are listed as follows: Weibeisheng: 0 mg/kg, 0.1 mg/kg, 0.3 mg/kg, 1 mg/kg, and 3 mg/kg; omeprazole: 0 mg/kg, 0.3 mg/kg, 1 mg/kg, 3 mg/kg, and 10 mg/kg; hydrotalcite: 0 mg/kg, 1 mg/kg, 3 mg/kg, 10 mg/kg, and 30 mg/kg. The following indices were measured:

① ulcer index: the longest diameter in the length direction of an ulcer area and the longest diameter in the width direction perpendicular to the longest diameter in the length direction of the ulcer area were measured by a vernier caliper, and the product of the above two diameters is the ulcer index.

② ulcer inhibition rate: it represents the inhibition effect of a drug on the ulcer index. The calculation formula: ulcer inhibition rate=(average value of ulcer indices in the model group−average value of ulcer indices in the drug groups/average value of ulcer indices in the model group)×100%.

Experiment Example 4

Prevention of the Recurrence of Acetic-Acid Induced Chronic Gastric Ulcers in Rats by Using the pH Buffered Bioactive Glass In this study and experiment, we evaluated the preventive effect of the tested drug (namely, the bioactive glass) on the recurrence of chronic gastric ulcers by adopting the rat model of IL-1β-induced recurrence of acetic-acid induced chronic gastric ulcer, and using omeprazole as the control. The results indicated that the preventive effect of 3 mg/kg of the bioactive glass (Production Example 10) on the recurrence of chronic gastric ulcers is equivalent to that of 10 mg/kg of omeprazole, both being 50%.

Conclusion: The bioactive glass has a good preventive effect on the IL-1β-induced recurrence of acetic-acid induced chronic gastric ulcers in rats, which is equivalent to the preventive effect of omeprazole, with the inhibition rates thereof both reaching 50%.

Supplement—Rat Model of Acetic-Acid Induced Chronic Gastric Ulcer Recurrence:

The model of acetic-acid induced chronic gastric ulcer was first copied here: After fasting for 24 hours, the rats were anesthetized and disinfected in a conventional way, and then was cut from the xiphoid down along the medioventral line to about 2 cm, so as to remove the stomach from the enterocoelia; 5 μl of 100% glacial acetic acid was injected by using a microsyringe into a position close to the muscular layer below the anterior wall serosa of the gastric antrum; when a translucent white spot with a diameter of about 3 mm appeared, the stomach was given back to the enterocoelia, and was enveloped in omentum majus; then, peritoneum, muscular layer and skin were sutured in this order. 90 days after the injection of acetic acid, a model of gastric ulcer recurrence was copied by intraperitoneal injection of 1 μg/kg of IL-1β according to the method described in "Role of neutrophils in a rat model of gastric ulcer recurrence caused by interleukin-1 beta", T. Watanabe, T. Arakawa, T. Fukuda, K. Higuchi, and K. Kobayashi, *Am J Pathol,* 1997, 150: 971-979 . As to the model non-recurrence group, normal saline was intraperitoneally injected in the same volume. 48 hours later, the animals were killed (fasting for 24 hours before killed).

Group and administration: after the injection of acetic acid, the rats with chronic gastric ulcers were randomly divided into 4 groups, namely, model non-recurrence group, model recurrence group, omeprazole group, and tested drug, bioactive glass group. Each group had 8 rats, which were raised conventionally until the injection of acetic acid. 81 days after the injection, drugs were administered to the rats. To the omeprazole group (10 mg/kg/d) and the bioactive glass group (3 mg/kg/d) (Production Example 10), the corresponding drug suspensions were intragastrically administrated once a day, and to the model non-recurrence group and the model recurrence group, normal saline (pH: 8.0) was administered in the same volume instead. The administration lasted for 7 days. When the administration was completed, 1 μg/kg of IL-1β was intraperitoneally injected to the rats in each group to induce recurrence of ulcers, except the model non-recurrence group, in which normal saline was intraperitonealkly injected to the rats in the same volume. 48 hours later, the animals were killed (fasting for 24 hours before killed), and the stomach thereof were cut out for observation.

Experiment Example 5

Comparative Experiment on Inhibition Effect of the pH Buffered Bioactive Glass on Stress-Induced Gastric Ulcers Versus the Representative Drug (These Two Inhibition Effects are Equivalent)

This experiment was conducted in the same way as described in Experiment Example 2 . Different doses of omeprazole (0 mg/kg, 3 mg/kg, 10 mg/kg, 30 mg/kg and 100 mg/kg), hydrotalcite (0 g/kg, 0.1 g/kg, 0.3 g/kg, 1 g/kg and 3 g/kg), and Weibeisheng (0 g/kg, 0.05 g/kg, 0.15 g/kg, 0.5 g/kg and 1.5 g/kg) were intragastrically administrated to the mice. Two hours later, the mice were subjected to stress in water at 21±1° C. for 15 hours (the drug was administered to the Weibeisheng group again two hours before the end of stress). The animals were then killed and autopsy was performed. The results indicated that in each solvent control group, the incidence rate of ulcer was 100%, and the ulcers were mainly represented in punctate bleeding, and represented in strip bleeding in a few animals. In a normal mouse, the gastric mucosa is even and smooth and the color thereof is milk-white. In the mice of the solvent groups, as compared with a normal mouse, the gastric mucosa is not smooth, inflammatory red swellings are present on the gastric wall, and the gastric wall is obviously thickened. Omeprazole, hydrotalcite and Weibeisheng all can inhibit occurrence of ulcers and are dose-dependent. As seen from the general observation of the stomach (smoothness of the gastric mucosa, color of the gastric wall and inflammation), there is no obvious difference between the effect of Weibeisheng and that of each positive drug. Regarding the inhibition rate, Weibeisheng has an inhibition effect on mouse stress-induced gastric ulcers slightly better than that of hydrotalcite and inferior to that of omeprazole. After the ulcer index of each group was scored, the inhibition effect of each drug on mouse stress-induced gastric ulcers (namely, the maximum inhibition rate $E_{max}$) was calculated. See Table 4 below:

TABLE 4

The maximum inhibition rate $E_{max}$ of tested drugs on mouse stress-induced gastric ulcers

| Stress ulcers | Omeprazole | Hydrotalcite | Bioactive glass |
|---|---|---|---|
| $E_{max}$ (% inhibition rate) | 64.8 | 43.7 | 60.2 |

The bioactive glass formulations (also named Weibeisheng) used in the above Experiment Examples 2 and 5 were prepared from Production Example 1 and a Tris buffer solution in a certain ratio. The ratios used in these two Experiment Examples were determined according to the weight of the mouse and the amount of intragastric administration.

The invention claimed is:

1. A pH buffered bioactive glass, characterized in that said pH buffered bioactive glass is a composition A comprising a bioactive glass and solid acidic particles, wherein said bioactive glass comprises $SiO_2$, $CaO$, $Na_2O$ and $P_2O_5$ as the raw materials, the content of each raw material in said composition A is measured by "part by mass", Composition A: $SiO_2$–40 to 60; CaO–15 to 30; $Na_2O$–15 to 30; $P_2O_5$–2 to 8; Solid acidic particles–3 to 7;

wherein the pH of the composition A in a liquid is 8.0±0.3.

2. The pH buffered bioactive glass according to claim 1, characterized in that said pH buffered bioactive glass is a tablet, a capsule or a suspension.

3. The pH buffered bioactive glass according to claim 1, characterized in that said solid acidic particles are solid citric acid particles.

4. The pH buffered bioactive glass according to claim 2, characterized in that said solid acidic particles are solid citric acid particles.

5. The pH buffered bioactive glass according to claim 3, characterized in that said composition A is a tablet or a capsule.

* * * * *